United States Patent [19]
Kampen

[11] Patent Number: 5,177,009
[45] Date of Patent: Jan. 5, 1993

[54] PROCESS FOR MANUFACTURING ETHANOL AND FOR RECOVERING GLYCEROL, SUCCINIC ACID, LACTIC ACID, BETAINE, POTASSIUM SULFATE, AND FREE FLOWING DISTILLER'S DRY GRAIN AND SOLUBLES OR A SOLID FERTILIZER THEREFROM

[76] Inventor: Willem H. Kampen, 447 Blue Rock Dr., Charlotte, N.C. 28213

[21] Appl. No.: 381,179

[22] Filed: Jul. 18, 1989

Related U.S. Application Data

[63] Continuation-in-part of Ser. No. 136,415, Dec. 22, 1987, abandoned.

[51] Int. Cl.⁵ .............................................. C12P 7/20
[52] U.S. Cl. .................................... 435/139; 435/145; 435/146; 435/159; 435/161
[58] Field of Search ............... 435/139, 141, 145, 146, 435/159, 161, 163

[56] References Cited

U.S. PATENT DOCUMENTS

| | | | |
|---|---|---|---|
| 4,287,305 | 9/1981 | Compere et al. | 435/176 |
| 4,336,335 | 6/1982 | Muller et al. | 435/161 |
| 4,359,430 | 11/1982 | Heikkila et al. | 260/501.13 |
| 4,578,353 | 3/1986 | Assarson et al. | 435/165 |
| 4,689,048 | 8/1987 | Fortsch et al. | 210/650 |
| 5,019,263 | 5/1991 | Haag et al. | 210/500.25 |

OTHER PUBLICATIONS

"The Merck Index," 10th Ed., Merck & Co., Inc., Rahway N.J. pp. 1189, 4347, 5172 and 8746-1983.
Puspito et al., CA 86:122152, 1985.
Burris, "Recovery of Chemicals such as Glycerol, Dextrose, and Amino Acids from Dilute Broths", Int. Conf. Fuels Alc. Chem from Biomass, Nov. 10-12, 1986, Miami Beach, Fla.

Primary Examiner—Robert J. Warden
Assistant Examiner—Timothy M. McMahon
Attorney, Agent, or Firm—Rhodes, Coats & Bennett

[57] ABSTRACT

This invention relates to the manufacture of ethanol and the recovery of such by-products therefrom as glycerol, betaine, succinic and lactic acid, potassium sulfate and a free flowing distiller's dry grain and solubles useful as an animal feed or a component of food for humans or as a premix for agricultural fertilizer. The process disclosed is an improvement over that of U.S. application Ser. No. 136,415 in the area of enhancement of glycerol recovery from stillage resulting from the fermentation of a biomass mash, and involves production of glycerol in amount in excess of 10 grams per 100 grams of reducing sugar in the starting biomass mash.

13 Claims, 1 Drawing Sheet

PROCESS FOR MANUFACTURING ETHANOL AND FOR RECOVERING GLYCEROL, SUCCINIC ACID, LACTIC ACID, BETAINE, POTASSIUM SULFATE, AND FREE FLOWING DISTILLER'S DRY GRAIN AND SOLUBLES OR A SOLID FERTILIZER THEREFROM

RELATED APPLICATIONS

This application is a continuation in part of copending Application Ser. No. 136,415 filed Dec. 22, 1987 now abandoned, the priority of which is claimed.

FIELD AND BACKGROUND OF INVENTION

This invention relates to the manufacture of ethanol, and the recovery, as by-products thereof, glycerol, betaine, succinic and/or lactic acid, potassium sulfate and a free flowing distiller's dry grain and solubles useful as a food for animals or humans or as a premix for agricultural fertilizer.

The manufacture and/or recovery of all of the products named has been known heretofore, and all have commercial uses. Ethanol is used as a beverage, a chemical, and a fuel derived from renewable resources, and is typically manufactured by fermentation and distillation processes starting from biological materials such as corn, wheat or other grain, sugar cane or beets, grapes or other fruit, potatoes, cassava, sweet sorghum or the like. Glycerol, while known to be produced as a by-product of ethanol fermentation and distillation processes, has been manufactured commercially only by processes which have soap as the primary product or which synthesize glycerol from petrochemical feedstocks. Betaine is produced synthetically or from liquors of beet molasses. Succinic acid is synthesized from maleic or acetic acid or produced by means of a highly specific fermentation. Lactic acid is produced by fermentation with *Lactobacillus delbrueckii, B. dextrolacticus* or similar microorganisms. Potassium sulfate is usually obtained by reacting sulfuric acid with potassium chloride. Potassium chloride usually occurs in nature as the mineral sylvine or sylvite. Distiller's dry grain, characterized as with or without solubles, is conventionally produced as a by-product of fermentation and distillation processes, and is usually sufficiently infused with sticky by products such as glycerol as to have poor flowing qualities and be difficult to handle. If the substrate from which distillates are produced is a sugar cane or beet material, then the residue is typically used only as a liquid fertilizer or treated as a waste.

The manufacture of ethanol is sufficiently well known that the interested reader is referred to the available literature for descriptions of the basic processes. The manufacture of glycerol is, by way of example, discussed in Hildebrandt U.S. Pat. No. 2,160,245; Wallerstein U.S. Pat. 2,400,859; and Frankel U.S. Pat. No. 2,772,207, to which the interested reader is referred. The manufacture of succinic acid and free flowing distiller's dry grain by processes such as those to be described hereinafter has not, insofar as is known to the present inventor, been described in any prior patent other than that which has resulted from the aforementioned priority application.

The processes and apparatus of the present invention contemplate the production of each or all of the products mentioned in a commercially feasible manner in a fermentation and distillation or similar process.

BRIEF DESCRIPTION OF INVENTION

More particularly, it is an object of this invention to produce glycerol as a valuable co-product of a fermentation process such as may produce ethanol. In realizing this object of the present invention, the efficiency of the known ethanol producing fermentation and distillation processes is essentially maintained, while an additional valuable product is derived. More particularly, ethanol production follows known and widely published pathways of biochemical reactions. The present invention contemplates imposing pressures on such pathways in ways which result in enhanced generation of glycerol and succinic acid, and has determined that such enhancement is achieved with relatively little if any reduction of efficiency in the production of ethanol.

Likewise, a further object of this invention is the manufacture of betaine or betaine-HCl as a co-product of a fermentation from a substrate of sugar beets or similar materials.

Yet a further object of this invention is the recovery of lactic acid from those fermentation processes, such as wet milled corn and certain wine fermentations, where lactic acid is produced in substantial quantities.

BRIEF DESCRIPTION OF DRAWING

Some of the objects of the invention having been stated, other objects will appear as the description proceeds, when taken in connection with the accompanying drawing, in which a schematic representation of the flow of materials in the processes and apparatus of the present invention is shown.

DETAILED DESCRIPTION OF INVENTION

Figure 1:
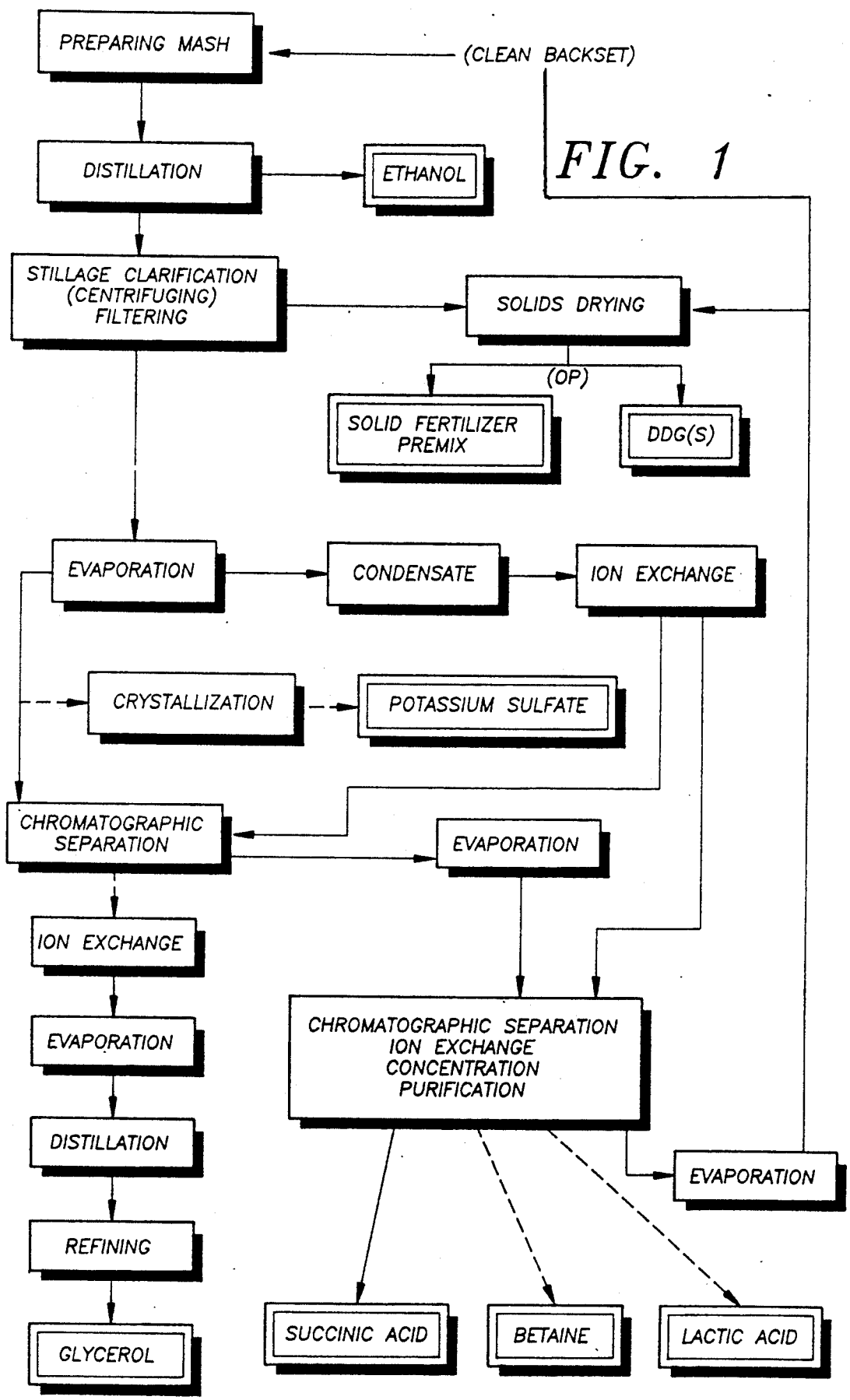

While the present invention will be described more fully hereinafter with reference to the accompanying drawing, in which a preferred embodiment of the present invention is shown, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

Referring now more particularly to the drawing accompanying this disclosure, the drawing represents certain steps and apparatus which, in the sequence disclosed hereinafter, accomplish the objects of this invention. Certain steps and apparatus, being well known to those having skill in the relevant arts, have not been shown but will be described for the reader.

It is known that the formation of ethanol in a fermentation process with yeast cells or other microorganisms is growth associated and that the formation of glycerol and succinic acid is interrelated. More specifically, in the Embden-Meyerhof pathway, NADH from triose phosphate oxidation exceeds the rate of acetaldehyde reduction, thus accounting for normal glycerol formation when the cell starved for ATP from glycolysis shifts excess NADH to the reduction of dihydroxyacetone phosphate to glycerol. Additional NADH is supplied through the Kreb's citric acid cycle. As used herein, NADH refers to nicotinamide adenine dinucleotide and ATP to adenosine triphosphate. In a well run fermentation process without the recycle of stillage, some 48 grams of ethanol, 4.0 grams of glycerol, 0.6 gram of succinic acid, and small quantities of lactic acid are formed per 100 grams of reducing sugar consumed. Ethanol producers using a corn wet milling process generally have substantial quantities of lactic acid present in their fermented mash, as do certain wine and other fermentations.

The commercially feasible recovery of the glycerol and succinic acid constituents, resulting in the production of free flowing DDG and/or DDGS, has been disclosed in the aforementioned priority application which is hereby incorporated herein by reference, and the present invention contemplates the further enhancement of the production of the by-products to be recovered and the recovery of additional by-products not contemplated by the previously disclosed invention. The processes by which such further enhancement and additional products are obtained and the result of operation in accordance with the present invention will be discovered from comparison of the processes given by the examples in the prior specification and those now to be described.

EXAMPLE 1

A mash prepared of ground degerminated yellow dent number two corn was cooked and liquefied to a dextrose equivalent (DE) of 21.3. The mash was then partially saccharified and subsequently fermented with co-immobilized gluco-amylase and Saccharomyces cerevisiae yeast with the following process parameters and yields:

|  | Batch | | |
| --- | --- | --- | --- |
|  | A | B | C |
| Process Parameter |  |  |  |
| YCC | 118 | 15 |  |
| DE at start of ferm. | 82 | 84 | 21 |
| Recycle | 83 | 84 | 40 |
| Temperature | 38 | 39 | 34 |
| pH | 6.8 | 7.2 | 5.0–3.9 |
| Head | 15.6 | 16.0 | atmos. |
| Time | 7.4 | 7.9 | 49 |
| Yields grams/100 grams RS |  |  |  |
| Ethanol | 43.9 | 43.1 | 47.9 |
| Glycerol | 17.0 | 20.2 | 9.1 |
| Succinic acid | 1.8 | 1.9 | 0.8 |
| Lactic acid | trace | trace | 11.9 |

In the table, YCC refers to yeast cell concentration in grams per liter with approximately $10^{10}$ cells per gram. DE refers to dextrose equivalent. Recycle refers to the percentage of recycled stillage in the mash being processed. Temperature is the temperature of fermentation in degrees Celsius. The reference to pH is to the value at which pH was maintained during the first two thirds of the fermentation by the addition of sodium carbonate in the process of column A and sodium hydroxide/sodium sulfite in the process of column B. The "Head" was fermenter head pressure in psig. Time is in hours for fermentation.

The process of Column C differs from those of Columns A and B. The process of Column C was based on the production of ethanol from wet milled corn; fermentation was continuous, and pH was permitted to vary over time from a starting pH of 5.0 to an ending pH of 3.9.

Considering the tabulated examples together, it is noted that production of glycerol was substantially enhanced with relatively little adverse affect on ethanol production. It is possible to further enhance glycerol and succinic acid production, although ethanol production falls substantially as such further enhancement is achieved.

In the processes of this Example 1, the fermented mash is distilled to strip off ethanol. The bottoms or whole stillage is clarified to obtain a clear liquid. In the preferred process, cross flow microfiltration systems with organic and/or inorganic membranes having pore sizes in the range of from about 0.1 microns to about 10 microns are used to remove particulate matter. Such membranes will process hot stillage either as received or after centrifugation and/or filtration to remove coarser particles. Preferably, computer controlled backflushing (at high pressure if necessary) will allow for high on-line stream factors for the microfiltration modules and will in most cases eliminate the need for (harsher) chemical cleaning. Known filtration apparatus having the characteristics recited may be incorporated in the overall apparatus which is used in practicing this invention.

Microfiltration yields a concentrate which is further processed into DDG or DDGS, a feed product for animals or a component for human food products, or a fertilizer base to which may be added the by-product stream from chromatographic separation processes described hereinafter. The microfiltration permeate may, if necessary, be softened to remove divalent cations which could otherwise foul the downstream chromatographic separation resin(s).

The clarified stillage is next concentrated to as high a solids concentration as practicable. Due to the clarification, the overall heat transfer coefficients involved have been improved while scaling of heat exchange surfaces has been minimized. Where the fermentation substrate is a sugar beet product, cooling and/or addition of sulfuric acid will bring about the formation of potassium sulfate, which may be recovered through crystallization to yield yet another valuable by-product.

Chromatographic separation of the clarified, concentrated stillage then follows. In a preferred method and generally as disclosed in the priority application identified above, the material passes through an ion exclusion apparatus containing a suitable resin. Glycerol, as a non-ionized compound, is unaffected by the Donnan potentials and distributes itself freely inside the aqueous pore structure of the resin beads, while the ionic compounds pass around the beads and exit the apparatus first. Ion exclusion and exchange resins may be kept in the potassium monovalent form, which will maximize the separation between ionic and nonionic components as well as improve formation of potassium sulfate. Attainable glycerol recovery efficiencies are in the range of from about 80 percent to about 98 percent, and the purity of the recovered glycerol is in a range of from about 80 percent to about 98 percent as well.

The chromatographic separation apparatus may be a single or multiple column system used as a pulsed bed or a simulated moving bed in a continuous process. The condensate from any evaporators used in the process may be treated in a mixed bed ion exchanger and used as the desorbent, thus minimizing make up water requirements. Desorbent to recovered glycerol ratios are in the range of from about 10 to about 25. Such a system is in ionic equilibrium and does not normally require regeneration. The by-product stream, containing succinic and lactic acids, may be concentrated to as high a solids content as practicable and the succinic and lactic acids separated in a further chromatographic separator using either acid retardation or ion exclusion. The succinic acid stream is concentrated and the acid recovered through crystallization. Similarly, lactic acid may be recovered at this point by standard processes. Ion exchange of the product streams will in most cases improve product purity. Depending upon the resin, starting substrate and operating conditions used, betaine and glycerol may exit the chromatographic separation together. It is then necessary to use a following (smaller) chromatographic separation to produce a pure betaine stream from which betaine may be recovered with standard processes.

The glycerol product stream is concentrated in double effect LTV evaporators to approximately 85 percent dry solids. Feed forward systems employing a thermocompressor with high pressure steam or feed backward systems using greater quantities of lower pressure steam may be used. The concentrated crude glycerin may be neutralized before it is fed into the rectifying section of a high efficiency distillation column. Through evacuation and direct steam injection the column partial pressure is kept low to minimize glycerol decomposition. Glycerol leaves the evaporators for condensers, and then is deodorized with steam and bleached with granular activated charcoal. Consumption of charcoal is minimized due to the already relatively purified state of the glycerol feedstock. The product then passes through polishing filters and a cooler to produce ultra pure glycerin. The evaporation, distillation and refining equipment are known, as such, and is available with the inclusion of design improvements over conventional glycerin apparatus from G. Mazzoni SpA of Italy.

It is also contemplated for this invention that glycerol, succinic acid, betaine, potassium sulfate and a solid fertilizer may be produced from beet molasses stillage without the specific preparation of a stillage having enhanced levels of glycerol and succinic acid. Such a process is illustrated by the following:

EXAMPLE 2

Stillage from a plant producing ethanol from sugar beet molasses was processed through steps of microfiltration with 0.2 micron ceramic membranes; evaporation of the permeate to 60 weight percent solids; and crys followed by centrifugation, washing and drying of the crystals. Enhanced formation of glycerol was not pursued during the fermentation steps preceding distillation of ethanol. The centrate was then fed to a chromatographic separation (ion exclusion) system to yield a mixture of glycerol and betaine which was then concentrated to 75 weight percent solids and fed to a second, smaller chromatographic system to yield quite pure glycerol and betaine streams. The glycerol stream was then ion exchanged in a mixed bed to yield a 97.6 percent pure glycerol which was processed into ultra pure glycerol with Mazzoni equipment. The betaine stream was processed into pure betaine or betaine-HCl. The remaining stillage was concentrated and dried into a fertilizer pre-mix. Overall glycerol recovery was 88.5 percent and overall betaine recovery was 93.2 percent. Succinic acid was not recovered.

The concentration of key components in weight percent at intermediate stages was as follows:

|  | Total Solids | Suspended Solids | Glycerol | Betaine |
| --- | --- | --- | --- | --- |
| Stillage | 7.5 | 1.0 | 0.7 | 1.5 |
| Microfiltration Permeate | 6.5 |  | 0.7 | 1.5 |
| Evaporator Concentrate | 60.0 |  | 6.3 | 13.5 |
| After First Chromatographic Separation | 36.3 |  | 10.6 | 22.7 |
| Evaporator Concentrate | 75.0 |  | 22.0 | 47.0 |
| Glycerol Stream after Second Chromatographic Separation | 38.2 |  | 37.3 |  |
| Betaine Stream after Second Chromatographic Separation | 23.7 |  | 0.5 | 20.9 |

In the drawing and specifications there has been set forth a preferred embodiment of the invention and, although specific terms are used, the description thus given uses terminology in a generic and descriptive sense only and not for purposes of limitation.

What is claimed is:

1. A process for manufacturing ethanol and recovering glycerol as a by-product thereof comprising the steps of:
    preparing a biomass mash,
    fermenting the biomass mash with yeast to produce a fermented mash having at least about 9 grams of glycerol and 40 grams of ethanol per 100 grams of reducing sugar in the biomass mash,
    distilling the fermented mash for producing ethanol and stillage,
    clarifying the stillage produced from the distillation of the fermented mash by subjecting the liquid portion thereof to a cross-flow microfiltration system having inorganic membranes with pore sizes of 0.1 to about 10 microns,
    passing the clarified stillage through an ion exclusion material for separating glycerol from other constituents of the clarified stillage, and
    purifying the separated glycerol.

2. A process for manufacturing ethanol and recovering glycerol and betaine as by-products thereof comprising the steps of:
    preparing a biomass mash from sugar beets,
    fermenting the biomass mash with yeast to produce a fermented mash,
    distilling the fermented mash for producing ethanol and stillage,
    clarifying the stillage from the distillation of the fermented mash by subjecting the liquid portion thereof to a cross-flow microfiltration system having inorganic membranes with pore sizes of 0.1 to about 10 microns,
    subjecting the clarified stillage to chromatographic separation by passing the stillage through an ion exclusion material for separating glycerol and betaine from other constituents of the clarified stillage and then from each other, and
    purifying the separated glycerol and betaine.

3. A continuous process for manufacturing ethanol and recovering glycerol as by product thereof comprising the steps of:

preparing a biomass mash, and in a continuous process performing the steps of:

fermenting the biomass mash with yeast to produce a fermented mash having at least about 9 grams of glycerol and 40 grams of ethanol per 100 grams of reducing sugar in the biomass mash, distilling the fermented mash for producing ethanol and stillage, clarifying the stillage produced from the distillation of the fermented mash by subjecting the liquid portion thereof to a cross-flow microfiltration system having inorganic membranes with pore sizes of 0.1 to about 10 microns, 4. A continuous process for manufacturing ethanol and recovering glycerol as by-products thereof comprising the steps of:

preparing a biomass mash from sugar beets, and in a continuous process performing the steps of:

fermenting the biomass mash with yeast to produce a fermented mash, distilling the fermented mash for producing ethanol and stillage, clarifying the stillage produced from the distillation of the fermented mash by subjecting the liquid portion thereof to a cross-flow microfultration system having inorganic membranes with pore sizes of 0.1 to about 10 microns, subjecting the clarified stillage to chromatographic separation for separating a glycerol product stream from other constituents of the clarified stillage, and purifying the separated glycerol product stream.

5. A process according to one of claims 1 or claim 2 or claim 3 or claim 4 wherein the step of fermenting a biomass mash comprises the step of mixing with the mash yeast cells in a concentration in excess of 100 grams per liter.

6. A process according to one of claims 1 or claim 2 or claim 3 or claim 4 wherein the step of preparing a biomass mash comprises the step of preparing a biomass mash having a dextrose equivalent of at least about 80 and the step of fermenting comprises mixing yeast cells with the mash.

7. A process according to one of claim 1 or claim 2 or claim 3 or claim 4 wherein the step of fermenting comprises the step of maintaining the pH of the mash substantially constant during the first two thirds of the fermentation process.

8. A process according to one of claim 1 or claim 2 or claim 3 or claim 4 wherein the step of fermenting the biomass mash comprises producing a fermented mash having at least about 15 grams of glycerol and 40 grams of ethanol per 100 grams of reducing sugar in the biomass mash.

9. A process according to one of claims 1 or claim 2 or claim 3 or claim 4 wherein the step of fermenting a biomass mash comprises the steps of preparing immobilized yeast cells, and mixing the immobilized yeast cells with the biomass mash.

10. A process according to one of claim 1 or claim 2 wherein the step of clarifying further comprises centrifugally separating solids from liquid constituents prior to microfiltration.

11. A process for manufacturing ethanol and recovering at least two of glycerol, betaine, and succinic acid as by-products thereof comprising the steps of:

preparing a fermented mash from sugar beets, distilling the fermented mash for producing ethanol and stillage, clarifying the stillage produced from the distillation of the fermented mash by subjecting the liquid portion thereof to a cross-flow microfiltration system having inorganic membranes with pore sizes of 0.1 to about 10 microns, passing the clarified stillage through an ion exclusion material for separating glycerol and succinic acid and betaine one from another and from other constituents of the clarified stillage, purifying the separated glycerol, succinic acid, and betaine, and drying any stillage residue.

12. A process for manufacturing ethanol and recovering glycerol and lactic acid as by-products thereof comprising the steps of:

preparing the biomass mash, fermenting the biomass mash with yeast to produce a fermented mash having at least about 9 grams of glycerol and 40 grams of ethanol per 100 grams of reducing sugar in the biomass mash, distilling the fermented mash for producing ethanol and stillage, clarifying the stillage produced from the distillation of the fermented mash by subjecting the liquid portion thereof to a cross-flow microfiltration system having inorganic membranes with pore sizes of 0.1 to about 10 microns, and passing the clarified stillage through an ion exclusion material for separating glycerol and lactic acid one from another and from other constituents of the clarified stillage.

13. A process for manufacturing ethanol and recovering glycerol and betaine as by-products thereof comprising the steps of:

preparing a biomass mash from sugar beets, fermenting the biomass mash with yeast to produce a fermented mash, distilling the fermented mash for producing ethanol and stillage, clarifying the stillage produced from the distillation of the fermented mash by subjecting the liquid portion thereof to a cross-flow microfiltration system having inorganic membranes with pore sizes of 0.1 to about 10 microns, subjecting the clarified stillage to chromatographic separation by passing the stillage through an ion exclusion material for separating glycerol and betaine from the other constituents of the clarified stillage and then from each other, and purifying the separated glycerol and betaine.

* * * * *